United States Patent [19]
DeCarlo, Jr.

[11] Patent Number: 6,152,962
[45] Date of Patent: Nov. 28, 2000

[54] ACETABULAR CUP WITH PLUG FOR SCREW HOLES

[75] Inventor: Alfred F. DeCarlo, Jr., Stamford, Conn.

[73] Assignee: Depuy Orthopaedics, Inc., Warsaw, Ind.

[21] Appl. No.: 09/223,486

[22] Filed: Dec. 30, 1998

[51] Int. Cl.[7] ........................................ A61F 2/34
[52] U.S. Cl. ........................................ 623/22.34
[58] Field of Search .................. 623/18, 22, 23, 623/19, 20, 22.34

[56] References Cited

U.S. PATENT DOCUMENTS

| | | | |
|---|---|---|---|
| 5,314,487 | 5/1994 | Schryver et al. | 623/22 |
| 5,507,825 | 4/1996 | Frei | 623/22 |
| 5,571,198 | 11/1996 | Drucker et al. | 623/22 |
| 5,609,648 | 3/1997 | Oehy et al. | 623/22 |
| 5,645,606 | 7/1997 | Oehy et al. | 623/22 |
| 5,782,929 | 7/1998 | Sederholm | 623/22 |

*Primary Examiner*—Bruce Snow

[57] ABSTRACT

A plug for apertures in an acetabular cup is provided. The plug is particularly useful in plugging screw holes. The plug helps to prevent plastic particles from a plastic bearing seated within the cup, from migrating through the aperture into the bone cavity or acetabulum surrounding the acetabular cup.

1 Claim, 6 Drawing Sheets

6,152,962

ACETABULAR CUP WITH PLUG FOR SCREW HOLES

FIELD OF THE INVENTION

The present invention relates to plugs for dome screw holes in the metal cups of a two part acetabular cup system typically comprising a metal cup and plastic socket bearing.

BACKGROUND AND SUMMARY OF THE INVENTION

A two part acetabular prosthesis typically comprises a metal cup and a plastic socket bearing generally placed within the metal cup. In many of these metal cups, apertures or holes are provided to accept bone screws to screw the cup into the acetabulum to provide additional securement prior to placing the bearing in the cup. One issue with the apertures is that wear of the plastic bearings may generate minute particles that enter the acetabulum through these openings.

An aperture plug has been described in U.S. Pat. No. 5,549,694 where the plug comprises a domed disc that is inserted into a cylindrical aperture and then is deformed to seal the hole.

Screws are used to augment fixation of an acetabular cup to bone when for example the acetabulum bone is deficient. Generally, a surgeon will select a cup with no holes if no deficiencies are apparent, a cup with two holes, or in situations where bone deficiency is more serious, a cup with more screw holes.

The screw holes are typically shaped with a spherical opening followed by a narrowed portion and conical portion having an increasing diameter larger than the narrowed portion. Typically, the screw head is spherical and the screw shaft has a diameter smaller than the narrowed portion of the cup opening. This structure permits angular orientation of the screw within the screw hole. Thus, a surgeon is able to select a screw hole and then orient the screw to best locate healthy bone in which to anchor the screw.

The present invention provides an improved aperture plug adapted for use with certain types of apertures such as screw holes. The present invention provides a plug for use with a screw hole where the screw hole is shaped to receive and allow orientation of an augmentation screw with a spherically shaped screw head.

In a first embodiment, the plug of the present invention includes a first portion, preferably spherically shaped and sized to fit the spherical opening of the acetabular cup screw hole; a second portion, preferably cylindrical, adjacent the first portion and sized to fit through the narrowed opening of the hole; and a third portion, preferably a deformable disc adjacent the cylindrical portion that can be compressively locked within the hole to seal the hole. The disc portion has an undeformed maximum outside diameter, $D_o$, that is smaller than the Diameter $D_n$ of the narrowed opening and a diameter when deformed, $D_f$, that is greater than the diameter, $D_n$ of the narrowed opening. The disc is inserted from the spherical opening, through the cylindrical opening and is then deformed thereby locking the plug within the hole. In this way, migration of the particles through the aperture is believed to be avoided.

In another embodiment the plug of the present invention includes a spherically shaped rim portion sized to fit the spherical opening of the screw hole, a cylindrical portion adjacent the rim portion and a deformable expanded portion on the opposite side of the cylindrical portion from the rim portion. In one embodiment, the expanded portion comprises a plurality of axial slits that may be contracted to enable removal of the plug. A variation of this invention provides the deformable axial slits on the spherical rim portion as opposed to the expanded portion.

One aspect of various embodiments of the present invention may provide an acetabular cup with pre-plugged screw holes having removable plugs placed in the screw holes prior to use. In these various embodiments the plugs may be removed prior to or after implantation.

The plugs may be placed in the screw apertures of the acetabular cup prior to use and may then be removed as necessary when the physician believes additional securement with screws is desirable in a particular area of the acetabulum. One aspect of a preferred embodiment provides a plug-removing device, e.g., an instrument that engages the plug for removal.

DETAILED DESCRIPTION OF THE DRAWINGS

DETAILED DESCRIPTION OF THE INVENTION

FIGS. 1–5 illustrate a first embodiment of the invention.

Figure 1:
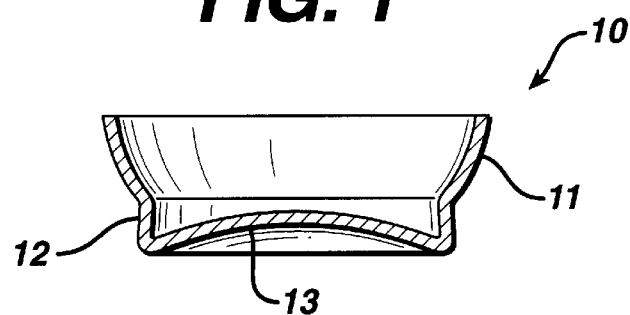
FIG. 1 illustrates a sectional view of the plug of the present invention prior to deformation of the plug.

Referring now to FIG. 1, there is illustrated a plug 10 of the present invention before deformation.

The plug 10 comprises a spherical rim portion 11 tapering to a cylindrical portion 12, and ending in a domed disc portion 13 adjacent the cylindrical portion 12.

The plug 10 is preferably made of a deformable, biocompatible material such as a plastic or metal. In a preferred embodiment, a soft, chemically pure titanium is used with a metal cup made of Ti-6A1-4V alloy. The plug 10 may be formed and drawn from a flat piece of metal having the shape of plug 10.

Figure 2:
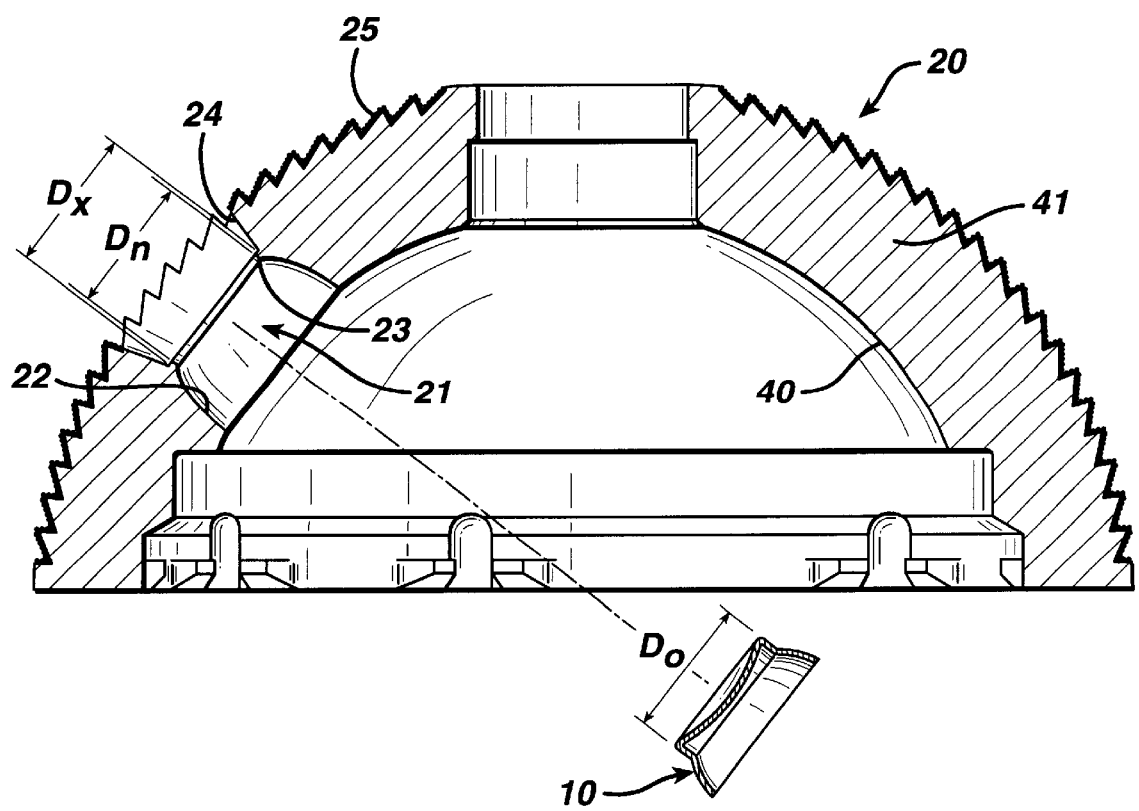
FIG. 2 illustrates an acetabular cup having screw holes.
Figure 3:
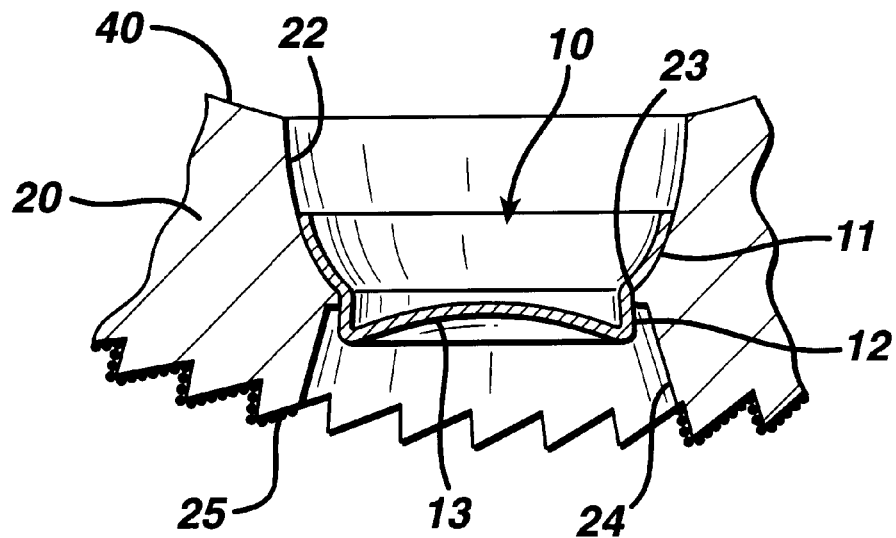
FIG. 3 illustrates a cross section of a metal cup with the undeformed plug of FIG. 1 inserted therein.
Figure 4:
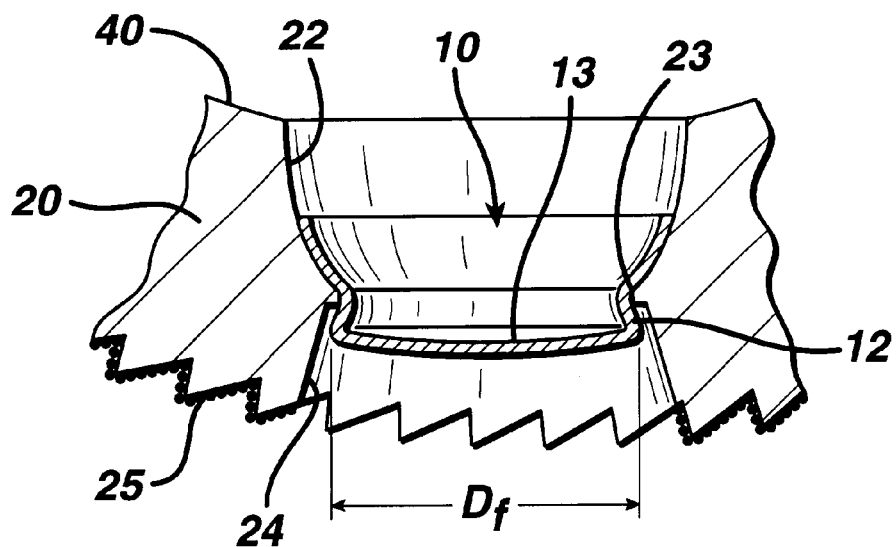
FIG. 4 illustrates a cross section of the plug of the present invention in an acetabular cup.

Referring now to FIGS. 2–4, there is illustrated a system of the present invention. An acetabular cup 20 for use with the plug 10 of the present invention. The acetabular cup 20 comprises a spherical outer shell 41 with an inner spherical portion 40 having at least one screw aperture 21. In FIGS. 3 and 4, the plug 10 is inserted into a screw aperture 21 of the acetabular cup 20. The aperture 21 has an internally located (i.e. towards the inner spherical portion 40 of the cup) spherically shaped opening 22, a narrowed cylindrical opening 23 having a diameter $D_n$, and an externally located (i.e. towards the external surface 25 of the cup 20) conically shaped conical opening 24. The diameter $D_n$ of the cylindrical opening 23 is smaller than the minimum diameter $D_x$ of the spherical opening 22 and the conical opening 24.

The spherical portion 11 of the plug 10 is shaped to fit within the spherical opening 22. The diameter of the conical portion 12 and the diameter $D_o$ disc portion 13 are each less than the Diameter $D_n$ of the narrowed opening 23 so that the disc 13 extends through the narrowed opening 23 and the spherical portion 11 sits on the surface of the cup 20 that forms the spherical opening 22.

Figure 5:
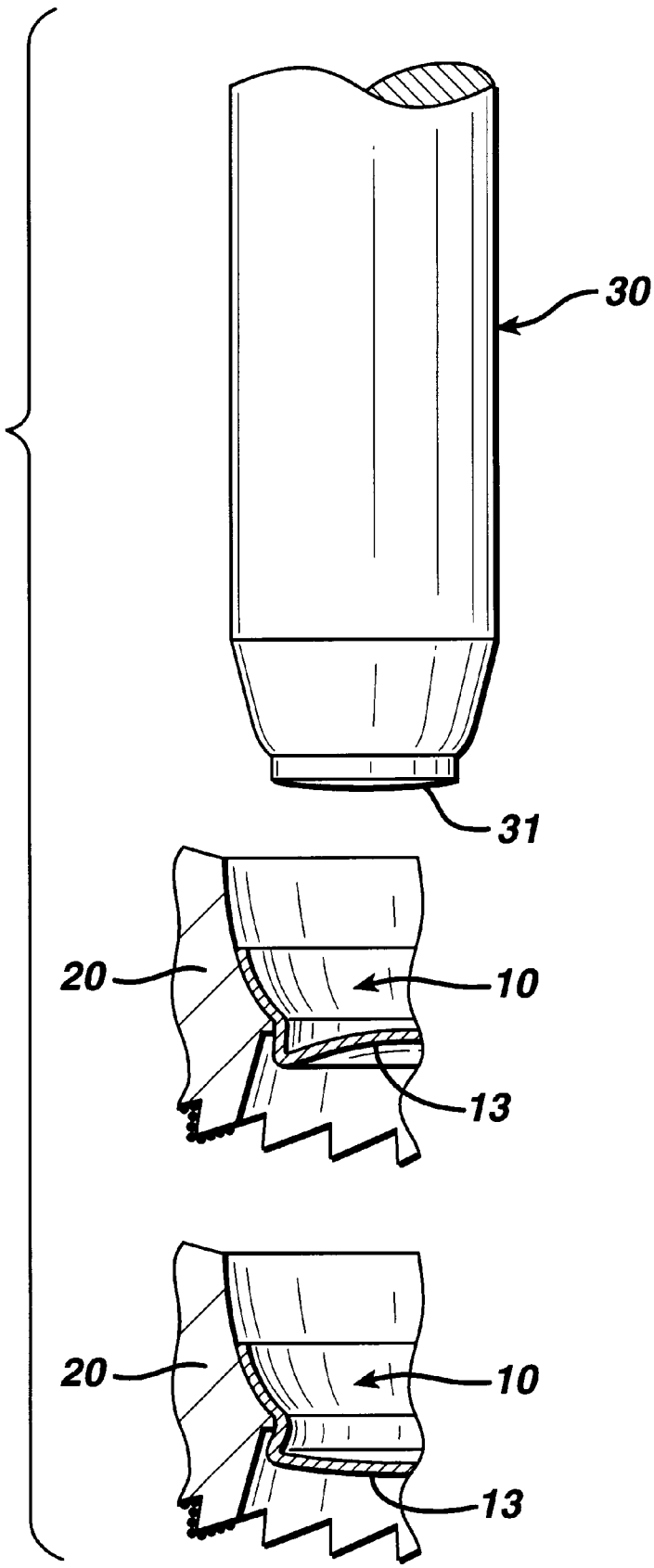
FIG. 5 illustrates a tool used to deform the plug with cross-sections of the plug before and after deformation.
Figure 6:
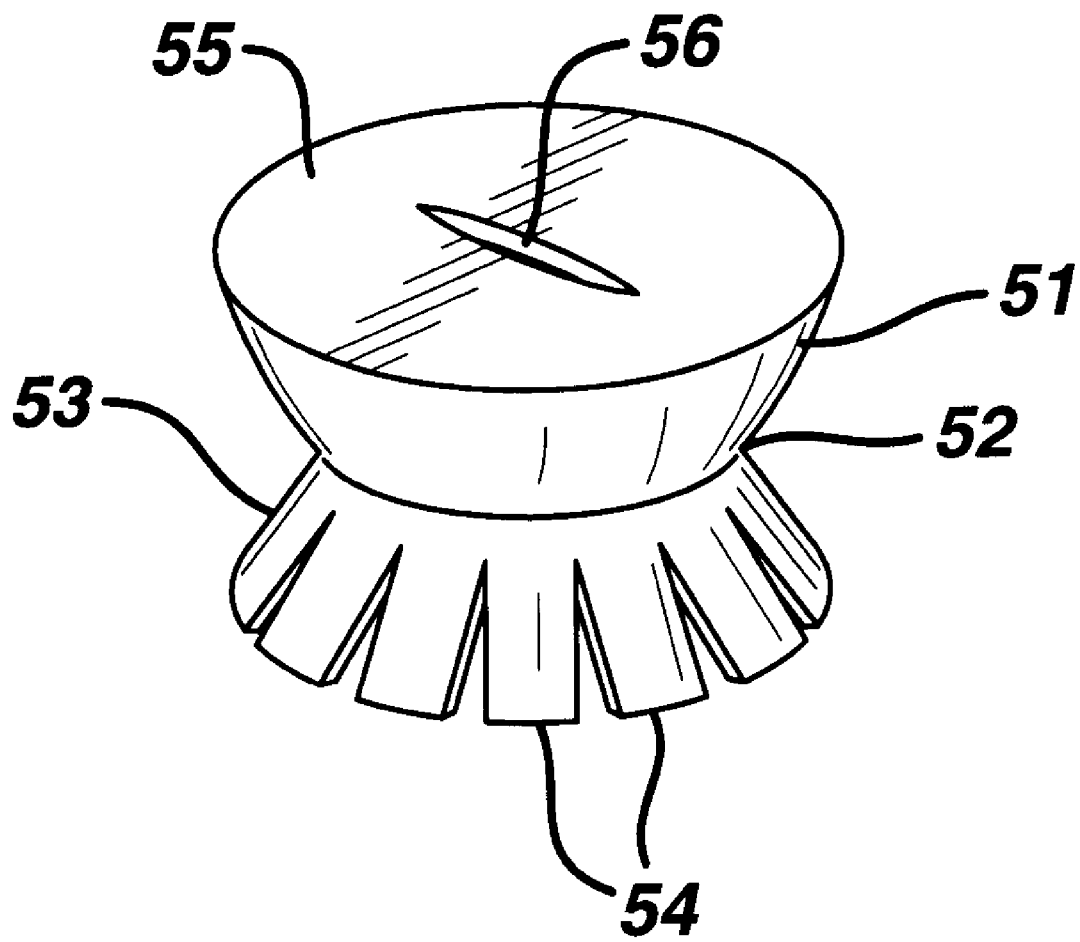
FIGS. 6–9 illustrate second and third embodiments of the present invention.

Referring now to FIG. 4, the plug 10 is illustrated in the aperture 21 deformed by the instrument 30 of FIG. 5. The instrument 30 includes an end 31 having a diameter $D_I$ smaller than the smallest inner diameter of the plug 10 and a shape generally the same as the spherical opening 22 and the narrowed opening 23 portions of the screw aperture 21. Once the plug 10 is placed in the aperture 21 as illustrated in FIG. 1 and the end 31 of the instrument is placed in the plug 10 and is used to deform the disc 13 in a direction towards the exterior of the cup 20. As illustrated in FIG. 4 the resulting diameter $D_f$ of the deformed disc 13 is greater than the diameter $D_o$ of the undeformed disc 13. Also, the disc 13 extends into the conical portion 24 of the aperture 21, which has a larger diameter than the narrowed opening 23 diameter $D_n$. The plug 10 in the deformed position engages three surfaces, the spherical opening surface 22, the narrow opening surface 23 and the conical opening surface 24.

Referring now to FIGS. 6–10 there is illustrated another embodiment of the present invention. Plugs 50, 50a comprise respectively a rim portion 51 ending on one end in a top 55, 55a having a coined slit 56, 56a extending only partially through the top 55 55a. The coined slit 56, 56a, will facilitate puncturing for removal with the plug remover 60 (FIG. 1c). The rim portion 51, 51a tapers to a cylindrical portion 52, 52a and end in a skirt portion 53, 53a including tabs 54, 54a extending outwardly.

Figure 7:
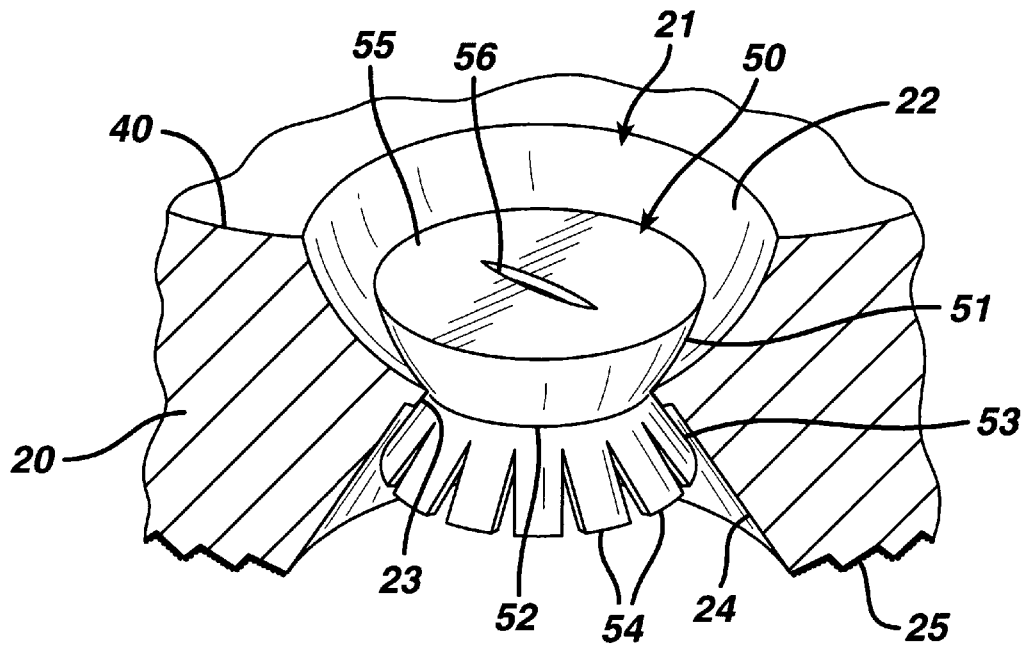

In use as illustrated in FIG. 7, the plug 50 is placed in the screw aperture 21 of the acetabular cup 20. The cup 20 maybe pre-assembled with plug 50 or a plurality of plugs with a plurality of screw apertures ready, for use in surgery. The rim portion 51 of the plug 50 is shaped to fit with the spherical opening 22 while the cylindrical portion 52 is located within the narrowed opening 23 and the skirt portion 53 is located within the conical opening 24.

Figure 8:
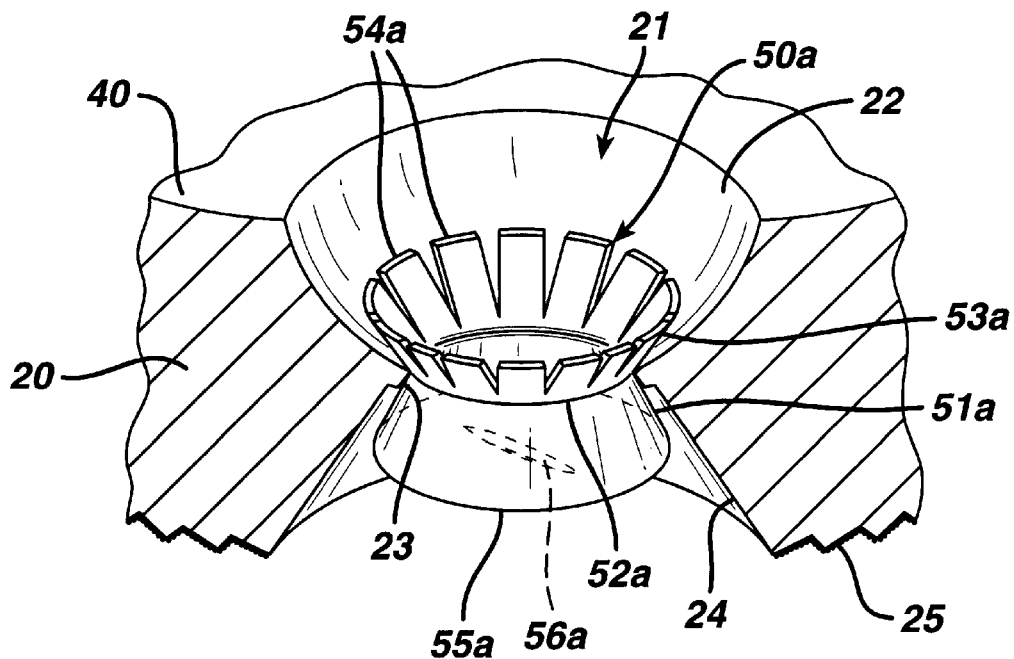

In use as illustrated in FIG. 8, the plug 50a is placed in the screw aperture 21 of the acetabular cup 20. The cup 20 may come preassembled with plug 50a inserted in the screw aperture 21 or a plurality of plugs may be placed in a plurality of screw apertures, ready for surgery.

The skirt 53a of the plug 50a is shaped to fit within the spherical opening 22 while the cylindrical portion 52a is located within the cylindrical opening 23 and the rim portion 51a is located within the conical opening 24.

The diameter of the skirt 53 or 53a and the rim portion 51 or 51a are initially greater than the diameter $D_n$ of the cylindrical opening 23 while the diameter of the cylindrical portion 52 or 52a are sufficiently small to permit the cylindrical portion to sit within the diameter of the narrowed opening 53.

Referring to FIG. 7, the skirt 53 is deformable so that the diameter of the skirt 53 is less than that of the narrowed opening 23 permitting removal from the screw aperture 21 from the side of the inner spherical portion 40 of the cup 20.

Referring to FIG. 8, the skirt 53a is deformable so that the diameter of the skirt 53 is less than that of the narrowed opening 23, permitting removal from the screw aperture 21 from the side of the external surface 25 of the cup.

Figure 10:
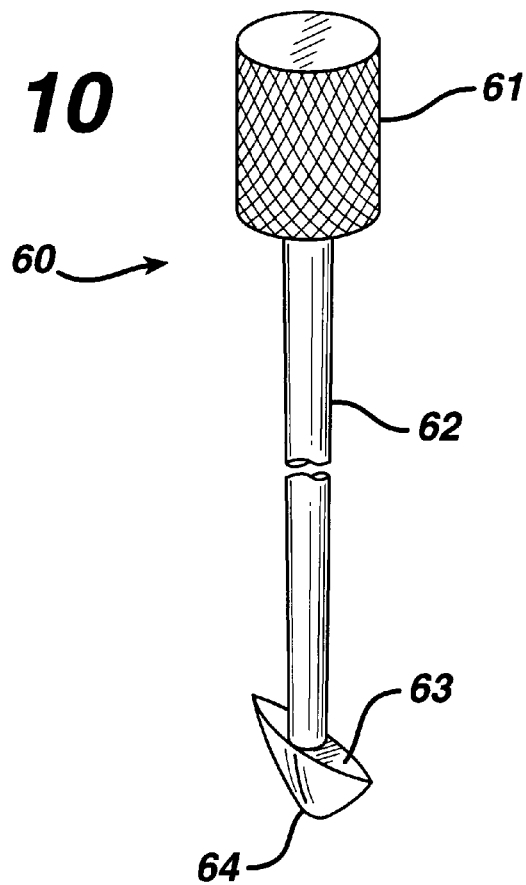
FIG. 10 illustrates a plug removal device.

FIG. 10 illustrates a plug remover 60, which can be used as part of the system of the present invention. The plug remover 60 comprises a handle 61 and harpoon 62 with an insertion end 63 having a tapered, pointed end 64.

Figure 9:
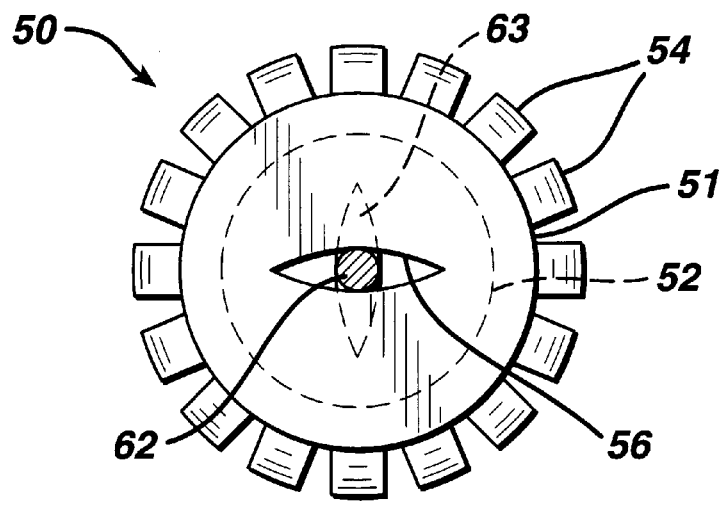

In use, the insertion end 63 of the plug remover 60 is inserted through the slot 56 or 56a in the end 55 or 55a of the plug 50 or 50a. FIG. 9 illustrates the instrument 62 of the plug remover 60 inserted through the slot 56 and rotated about 90°. The plug 60 may now be removed from the cup 20 by pulling on the handle 61 of the plug remover 60. The pulling force causes the tabs 54 of the skirt 53 to deform inward permitting the skirt 53 to pass through the narrowed opening 23 to remove the plug 50 from the cup 20.

The plug 50 in FIG. 7 may be removed prior to surgical placement of the cup 20 or after placement of the plug 50a may be removed prior to surgical placement because the plug is removed from the exterior side which when placed in a patient is not easily accessible.

The plug remover 60 may also be used where there are no slots 56 or 56a in the plug 10, 50, or 50a. The point 64 at the end 63 of the harpoon 62 may be used to puncture the plug 10, 50 or 50a. The remover 60 may then be rotated so that the end 63 engages the back or end of the plug 60.

Various embodiments and modifications may be made to the above-described embodiments without departing from the scope of the invention claimed herein.

The plugs 50, 50a are preferably made of a deformable biocompatible material such as a plastic or metal. In a preferred embodiment, a soft, chemically pure titanium is used with a metal cup made of Ti-6A1-4V alloy. The plugs 50, 50a may be formed and drawn from a flat piece of metal having the shape of plugs 50, 50a.

Although this invention is described with respect to a particular embodiment, it is to be understood that modifications can be made without departing from the spirit and scope of the invention as will be evident to those of ordinary skill in the art.

What is claimed is:

1. An acetabular cup for receiving a bearing, said cup comprising:

A body having an interior surface for receiving the bearing, an exterior surface for engaging bone, and an aperture which passes through the body from the interior surface to the exterior surface, said aperture having:

(a) a first portion, which is accessible from the interior of the body and has a cross-section having a first aperture diameter;

(b) a second portion, which is contiguous with the first portion, is located radially outward from the first portion and has a second aperture diameter that is smaller than said first aperture diameter; and (c) a third portion which is contiguous with the second portion and has a third aperture diameter that is larger than said second diameter; a deformable plug located within said aperture so as to seal the aperture, said plug comprising:

a first plug portion having a first plug diameter, greater than said second aperture diameter;

a second plug portion having a second plug diameter at least as small as said second aperture diameter; and a third plug portion comprising a deformable disc (i) which prior to insertion, said disc having a concave side, a convex side, and a diameter which is smaller than the first and third aperture diameters and is larger than the second aperture diameter (ii) said plug capable of being inserted into the aperture from the interior of the body, with said convex side oriented toward the interior of the body, and (iii) capable of being buckled as a result of having been deformed so as to have a convex portion oriented toward the exterior of the body;

wherein said first plug portion is located within said first portion of the aperture, said second plug portion is located in said second portion of the aperture, with said third plug portion located in said third portion of the aperture, said plug being thereby locked within said aperture.

* * * * *